United States Patent [19]

Hemmer et al.

[11] Patent Number: 5,531,685

[45] Date of Patent: Jul. 2, 1996

[54] STEERABLE VARIABLE STIFFNESS DEVICE

[75] Inventors: Chad G. Hemmer, Indianapolis; John A. Steen, Zionsville, both of Ind.; Michael R. Forman, St. Paul; Jonathan R. McGrath, Chanhassen, both of Minn.

[73] Assignees: Catheter Research, Inc., Indianapolis, Ind.; Schneider (USA) Inc., Minneapolis, Minn.

[21] Appl. No.: 284,076

[22] Filed: Aug. 1, 1994

Related U.S. Application Data

[63] Continuation-in-part of Ser. No. 76,113, Jun. 11, 1993, Pat. No. 5,334,168.

[51] Int. Cl.$^6$ .......................... A61M 37/00; A61M 25/00
[52] U.S. Cl. ................................ 604/95; 604/281
[58] Field of Search ..................... 604/95, 280–282; 600/143

[56] References Cited

U.S. PATENT DOCUMENTS

| | | |
|---|---|---|
| 3,868,956 | 3/1975 | Alfidl et al. . |
| 4,543,090 | 9/1985 | McCoy . |
| 4,601,705 | 7/1986 | McCoy . |
| 4,758,222 | 7/1988 | McCoy . |
| 4,777,799 | 10/1988 | McCoy et al. . |
| 4,790,624 | 12/1988 | Van Hoye et al. ................. 350/96026 |
| 4,799,474 | 1/1989 | Ueda .................... 604/281 X |
| 4,918,919 | 4/1990 | McCoy et al. . |
| 4,944,727 | 7/1990 | McCoy . |
| 4,950,258 | 8/1990 | Kawai et al. ............ 604/281 |
| 5,019,040 | 5/1991 | Itaoka et al. ............... 604/95 |
| 5,025,799 | 6/1991 | Wilson . |
| 5,055,101 | 10/1991 | McCoy . |
| 5,090,956 | 2/1992 | McCoy . |
| 5,114,402 | 5/1992 | McCoy . |
| 5,135,517 | 8/1992 | McCoy . |
| 5,143,085 | 9/1992 | Wilson . |
| 5,188,111 | 2/1993 | Yates et al. . |
| 5,211,183 | 5/1993 | Wilson . |
| 5,242,394 | 9/1993 | Tremulis .................. 604/95 |

FOREIGN PATENT DOCUMENTS

| | | | |
|---|---|---|---|
| 4028375 | 1/1992 | Japan ..................... 604/281 |
| 4051967 | 2/1992 | Japan ..................... 604/281 |
| 1204216 | 1/1986 | U.S.S.R. ....................... 604/281 |

*Primary Examiner*—John D. Yasko
*Assistant Examiner*—Adam J. Cermak
*Attorney, Agent, or Firm*—Barnes & Thornburg

[57] ABSTRACT

An apparatus includes a flexible tubular member containing a shape-memory tube formed to include a lumen extending along the central axis of the tubular member. A liner sleeve extends through the lumen of the shape-memory tube and lies inside the tubular member. A control system selectively heats the shape-memory tube to its activated state causing the shape-memory tube to move toward a predetermined shape if it is different than its present configuration. Whether the shape-memory tube moves or not, it will increase significantly in stiffness, both axial and bending to help retain, hold, or wedge the apparatus in place in a selected body cavity while catheters or other objects are passed through a lumen in the liner sleeve.

50 Claims, 4 Drawing Sheets

FIG. 3

STEERABLE VARIABLE STIFFNESS DEVICE

BACKGROUND AND SUMMARY OF THE INVENTION

This is a continuation-in-part of U.S. application Ser. No. 08/076,113, filed Jun. 11, 1993, now U.S. Pat. No. 5,334,168, issued Aug. 2, 1994.

The present invention relates to catheters, cannulae, and the like, and particularly to apparatus that are movable through body cavities and used to facilitate medical procedures on obstructions, organs, or tissue within the body. More particularly, the present invention relates to shape-memory elements for controlling steering and/or stiffness of medical devices, such as guide catheters, located within a body cavity.

A great deal of research effort has focused on providing a catheter having a distal end which, when inserted into a body, is readily steerable and aimable to advance the catheter through body cavities and passageways. It has been observed that materials exhibiting mechanical memory properties triggered by heat are particularly useful for enhancing the maneuverability of catheters or like devices. The materials are commonly called "temperature-activated memory materials" or "shape memory alloys" because they move to assume a predetermined shape when heated to a predetermined temperature.

Nitinol, a nickel-titanium alloy, is one such temperature-activated memory material that has been formed into memory element strips or tubes and deployed in the distal end of a catheter. Heating the nitinol memory element strips to a given temperature using an electric current provided by a power supply causes the memory elements to deform to assume a predetermined shape, thereby deflecting the distal end of the catheter. See, for example, U.S. Pat. Nos. 4,543,090; 4,601,705; and 4,758,222 for descriptions of known memory element systems for steering and aiming medical devices such as catheters, cannulae, and the like.

Various medical devices are used by doctors in surgery to guide instruments such as catheters, guide wires, balloon catheters, laser fibers, atherectomy catheters, ultrasound imaging catheters, angioscopic devices, and pressure-monitoring devices, etc., to remote regions inside the body of a patient. For example, during an intervention, a physician may need to unblock an occluded artery on a patient's heart using a balloon catheter. To accomplish this procedure, the physician must introduce a guide catheter into the body of a patient and use the guide catheter to guide the balloon catheter through the body to a particular destination in an occluded artery on the heart so that the balloon catheter is positioned to expand or inflate and thereby unblock the occluded region inside the artery.

Foreign matter, such as plaque, is known to accumulate on the interior walls of certain arteries and, over time, this accumulated foreign matter can occlude the artery and block the flow of blood and oxygen to various regions of the heart. This type of blood and oxygen flow disruption can lead to a heart attack. Unwanted plaque is known to accumulate in the coronary arteries and it is known to pass a coronary guide catheter through the aorta and into the ostium (opening) of the coronary arteries to reach an occluded region. See, for example, U.S. Pat. No. 5,195,990. Angiographic catheters are disclosed in U.S. Pat. Nos. 5,088,991 and 4,963,306.

Usually, another device is passed through the guide catheter to reach and perform diagnostic and/or therapeutic work on a stenosis. Frequently, when that other device, such as an angioplasty balloon catheter or atherectomy device, is pushed toward the lesion, that other device causes the guide catheter to back out of the coronary ostium.

An improved medical device that is operable to guide a coronary catheter or other device to a particular destination in a body and capable of being temporarily stiffened so that it is "anchored" or "wedged" or otherwise retained in place during surgery would avoid shortcomings of conventional guide catheters. Ideally, such a medical device should be flexible enough to move through body cavities and yet stiff enough to hold its shape and position in a body cavity once it arrives at its destination in the body. Typically, the design of conventional guide catheters reflects a compromise between stiffness and flexibility. What is needed is a flexible guide catheter that is controllable to become stiffer at the direction of the user once the guide catheter reaches its destination in the body of a patient and can later be unstiffened so that it is flexible enough to be removed easily following an intervention. This increased stiffness helps to retain, hold, or wedge the guide catheter in place in a body cavity (e.g., aorta and coronary ostium) during delivery of a balloon catheter or other element through the guide catheter to reach a region to be treated (e.g., occluded coronary artery) inside the body of the patient.

According to the present invention, an apparatus includes a flexible, elongated tubular member and a shape-memory tube. The tubular member has a central axis extending longitudinally therethrough and the shape-memory tube is formed to include a lumen extending along the central axis. A liner sleeve extends through the lumen of the shape-memory tube and lies inside the tubular member. Also, control means is provided for selectively heating the shape-memory tube to its activated state. Activated, the shape-memory tube may move toward its predetermined shape, if it is different than its present configuration. Whether the tube moves or not, the shape-memory tube will increase significantly in stiffness, both axial and bending. Advantageously, this added stiffness helps to retain, hold, or wedge the apparatus in place in a selected body cavity while other catheters or objects are passed through a lumen in the liner sleeve of the apparatus.

The control means includes first and second conductive coatings deposited on the liner sleeve and an insulator mounted to prevent establishment of an unwanted electrical connection between the shape-memory tube and either of the first or second conductive coatings. The control means also includes a first conductor passing through an opening in the insulator to establish one leg of a circuit path, which one leg electrically interconnects the first conductive coating and the shape-memory tube. The control means further includes a second conductor passing through another opening in the insulator to establish another leg of a circuit path, which another leg electrically interconnects the second conductive coating and the shape-memory tube.

Illustratively, in use, the shape-memory tube can be heated easily by passing an electric current along a circuit path through the first conductive coating on the liner sleeve, the first conductor, the shape-memory tube, the second conductor, and the second conductive coating also on the same liner sleeve. The apparatus or guide catheter is very flexible as it is being moved through the body to reach its destination because the shape-memory tube is relatively cool and is below its transition (activation) temperature. However, once the apparatus arrives at its destination in a body cavity, the physician operates the control means to heat the shape-memory tube using electricity conducted through the circuit path. Once heated, the shape-memory tube assumes a stiff predetermined shape. The stiffness of the shape-memory tube is due to a modulus change caused by heating the shape-memory tube. This causes the tubular member surrounding the shape-memory tube to become stiff to help anchor, wedge, or otherwise fix the apparatus in a desired position inside a body. In some instances, the shape-memory tube will move when heated, in other cases it will not move when heated.

In one application, the tubular member is sized to reach into the right coronary artery and the shape-memory tube can be heated by remote control to "stiffen" the tubular member once the outlet of the tubular member is inserted into the right coronary ostium. This stiffens the guide catheter so that it is hardened, lodged, wedged, or otherwise anchored to remain in a fixed position in the aortic arch of a heart patient. Once anchored, other elements can be passed through the guide catheter to reach into the right coronary artery to unblock the occluded region.

Additionally, a device which is selectively stiffenable can be made more flexible upon completion of the interventional procedure, thereby making it easier to disengage from the ostium and less traumatic to the surrounding tissue as it is removed. This is an advantage over present guide catheters which have been shaped and fabricated to provide maximum back-up support.

In preferred embodiments, the first conductive coating is applied to about one half of the exterior surface of the cylindrical liner sleeve and resembles a cylinder cut in half along its length. Likewise, the second conductive coating has a similar hut-like shape and is applied to the other half of the exterior surface of the cylindrical liner sleeve so that it does not contact the first conductive coating. The insulator lies inside the lumen of the shape-memory tube and extends around the two conductive coatings deposited on the exterior of the liner sleeve. The first conductor is positioned to lie in a first aperture formed in the insulator and the second conductor is positioned to lie in a second aperture formed in the insulator. This preferred arrangement provides a compact and easily manufactured means for heating the shape-memory tube to selectively stiffen an otherwise flexible guide apparatus.

Advantageously, the improved apparatus is stiffened using a nitinol shape-memory tube instead of solid core nitinol strips or rods. This apparatus is easy to manufacture and assemble. It will be understood that nitinol strips or rods could be used in an apparatus in accordance with the present invention.

Additional features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
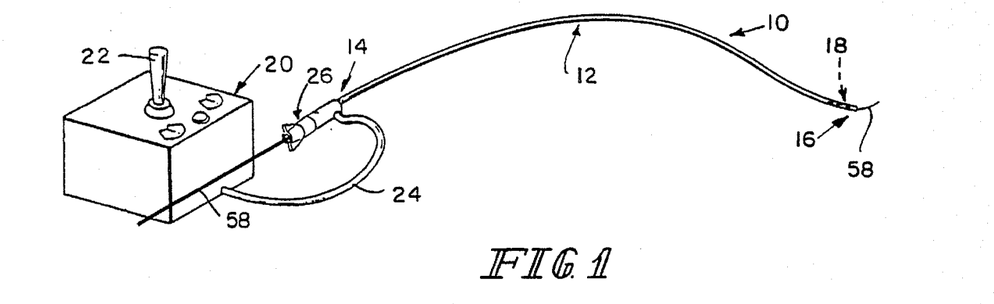
FIG. 1 is a perspective view of an apparatus in accordance with the present invention showing a guide catheter, a guide wire passing through the guide catheter, and a control unit for heating a temperature-activated shape-memory element mounted in the guide catheter.

An apparatus 10 embodying the present invention is shown generally in FIG. 1. Apparatus 10 includes an elongated tubular member 12 having a proximal end 14 and a stiffenable distal end 16. A shape-memory tube 18 made of nitinol (nickel titanium) or other suitable shape-memory alloy is mounted inside the stiffenable distal end 16 of tubular member as shown, for example, in FIGS. 2–4.

The apparatus 10 further includes an electronic control system 20 for controlling electric current flow to vary the temperature of the temperature-activated nickel titanium shape-memory tube 18 from a position external to the body so as to deflect the distal end 16 of the tubular member 12 in different directions corresponding to the preset shape of the shape-memory tube 18. Alternatively, a suitable control system could include other means for heating or cooling shape memory tube 18 such as: injection of hot or cold fluids (e.g., saline) into an apparatus like apparatus 10, RF induction, or IR irradiation.

The control system 20 includes a power supply source (not shown) which may be either AC or DC or RF energy. The system 20 also includes a control device 22 which, in the illustrative embodiment, is similar to a "joystick" control, tactile membrane switch, or ball controller. It will be appreciated that various types of control devices 22 may be employed without departing from the scope of the present invention. Reference is hereby made to U.S. Pat. No. 5,188,111 for more detailed descriptions of suitable control systems for guiding steerable and aimable apparatus. The '111 patent is incorporated by reference herein.

The power supply source is coupled through control device 22 to the tubular member 12 by cable 24 and a coupling device 26. Further, the temperature-activated shape-memory tube 18 is electrically connected to the control device 22 through cable 24 and coupling device 26 by an electrical wire (not shown) which is attached to the shape-memory tube 18 in the manner described below and shown in FIGS. 4–6. A return or ground wire (not shown) is also attached to the shape-memory tube 18.

Figure 2:
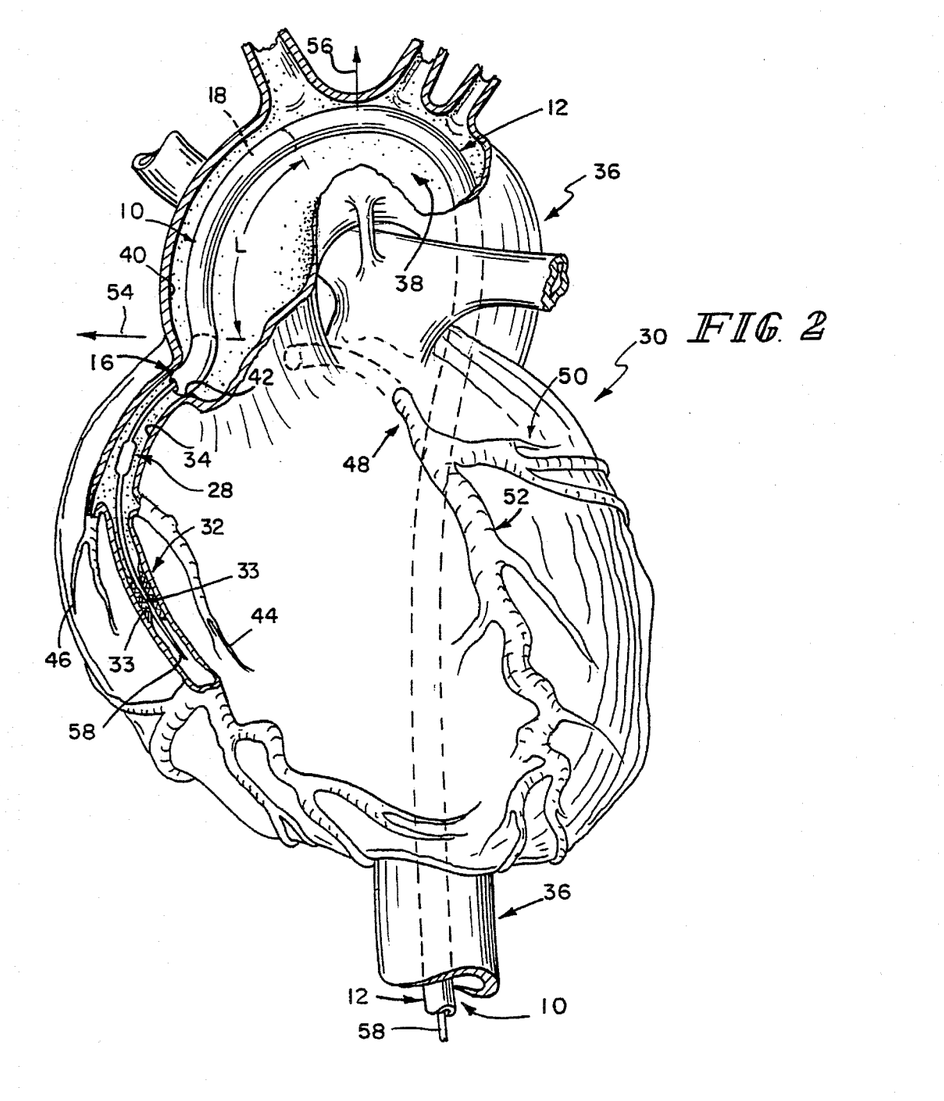
FIG. 2 is a view of a human heart, with portions broken away, showing an inactivated flexible guide catheter passing through the aortic arch and terminating in the right coronary ostium and a balloon catheter moving through the guide catheter toward a stenosis extant in the right coronary artery.
Figure 3:
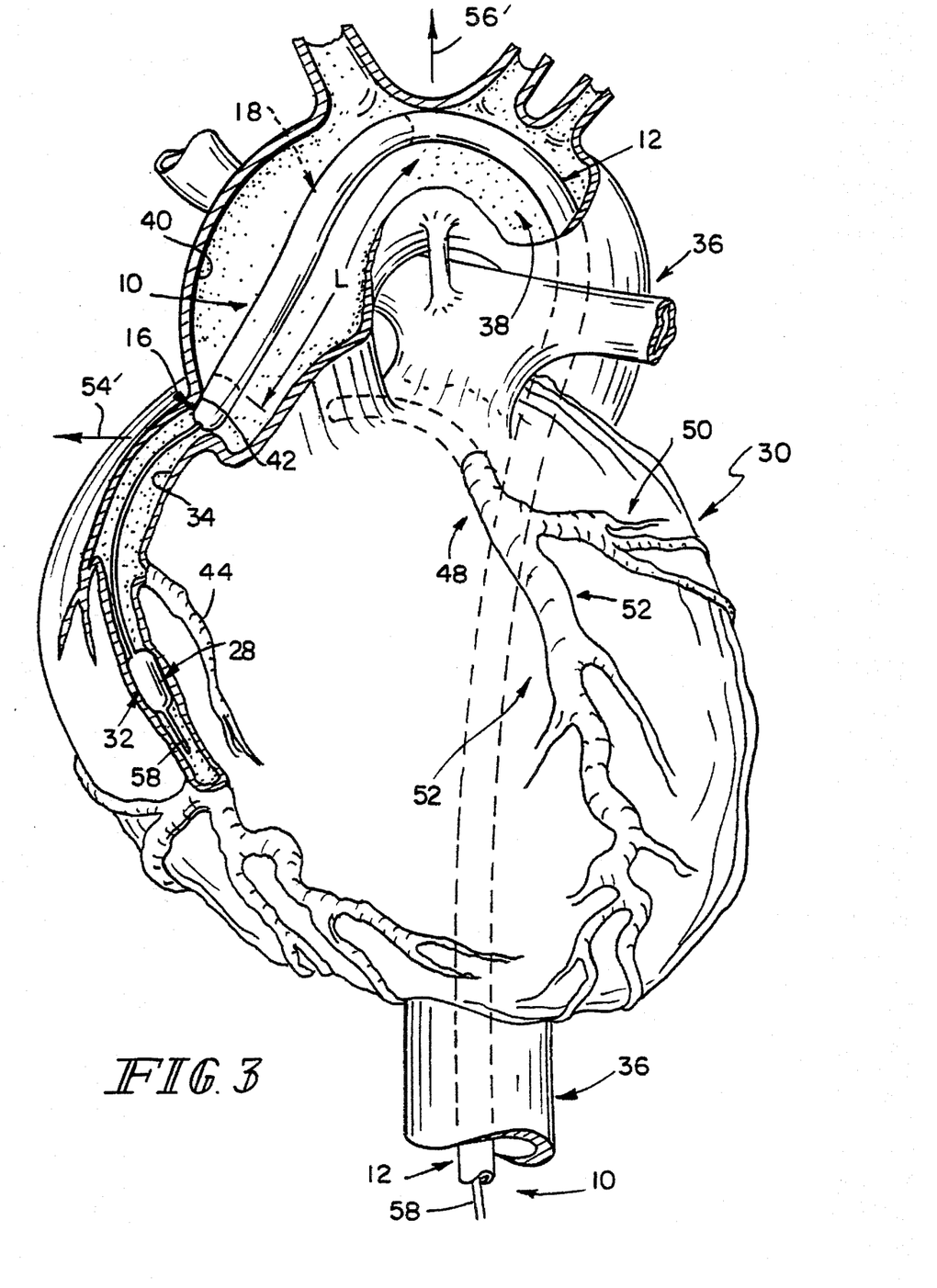
FIG. 3 is a view similar to FIG. 2 showing an activated "stiffened" guide catheter in an "anchored" or "wedged" position in the aorta following heating of the temperature-activated shape-memory element mounted in the guide catheter and showing a balloon catheter in an expanded or inflated condition in the formerly occluded region of the right coronary artery.

Shape-memory tube 18 is a temperature-activated shape-memory element that is isolated from body cavities shown in FIGS. 2 and 3 by insulative material (e.g., tubular member 12). The shape-memory tube 18 exhibits a memory characteristic in response to temperature changes. Instead of being a solid core wire or flat strip, shape-memory tube 18 preferably is formed in a tubular shape of a mechanical memory metal such as a nickel titanium alloy. While a nickel titanium alloy is desirable, other metal elements having a memory characteristic related to temperature could be used without departing from the scope of the invention. Such metal elements have a high resistance to electric current so that heat is produced when current is passed therethrough.

The shape-memory tube 18 has a first or preset shape (not shown) and a second shape (not shown). Preferably, the preset shape is an arcuate shape and the second shape is a straight shape. It will be appreciated that the preset shape could be any shape. Reference is hereby made to U.S. Pat. No. 4,944,727 for a more detailed description of suitable techniques for providing temperature-activated memory elements that are movable between arcuate and straight shapes. The '727 patent is incorporated by reference herein.

The temperature-activated shape-memory tube 18 is originally annealed into its preset shape. A preferred preset shape is a straight tube. During fabrication, the assembled catheter is heat-set (at a lower temperature than required to permanently change the preset shape of the shape-memory tube) to cause a specific shape set to occur in the inner and outer layers surrounding the shape-memory tube. During use, the application of energy to the shape-memory tube raises the temperature of the shape-memory tube, causing the shape-memory tube to stiffen and move the tube toward its preset shape. In the illustrative embodiment, the shape-memory tube 18 is then cooled and straightened to its second shape before incorporation into the distal end 16 of the tubular member 12. When the shape-memory tube 18 is again heated to a predetermined activation temperature, it returns to its preset shape. By applying an opposing force to a shape-memory tube 18 that has moved to assume its preset shape, it can be moved to a second shape. In the illustrative embodiment, the predetermined activation temperature is any temperature above body temperature. For example, the predetermined activation temperature may be in the range of 100° F. to 160° F. In other embodiments (not shown), the activation temperature may be lower than 100° F. For example, the activation temperature may be below 98.6° F. (e.g., human body temperature), thereby activating the shape-memory tube by the surrounding tissue and fluid upon insertion into the body of the heart patient. To deactivate the shape-memory tube, cooled saline could be infused through the guide catheter rendering the shape-memory tube flexible.

One application for apparatus 10 is shown in FIGS. 2 and 3. In this application, apparatus 10 functions as a guide catheter for guiding a balloon catheter 28 through arteries on and around a human heart 30 to reach an occluded region 32 containing accumulated plaque 33 in the right coronary artery 34 of heart 30. The guide catheter 10 passes upwardly through the descending aorta 36, around through the aortic arch 38, downwardly through the ascending aorta 40, and into the right coronary ostium 42 which is the inlet opening into the right coronary artery 34. The descending aorta 36 runs down through the thorax and abdomen (not shown) of the patient toward the common iliac arteries (not shown). Heart 30 also includes right coronary artery side branches 44 and 46, left main artery 48, left circumflex artery 50, and left anterior descending artery 52.

The guide catheter 10 is flexible as it is being inserted through the aorta 36, 38, 40 to position tip 16 in the right coronary ostium 42 as shown in FIG. 2. At this stage, the shape-memory tube 18 is relatively cool and it and the tubular member 12 are able to flex and bend and assume a wide variety of shapes during introduction of guide catheter 10 into the right coronary artery 42 of the heart 30.

As shown in FIG. 3, the distal end 16 of guide catheter 10 can be stiffened by heating shape-memory element 18 so that, in effect, the distal end 16 is "anchored" or "wedged" to assume a fixed position in the aortic arch 38 and the ascending aorta 40. This wedging action makes it easier for a physician to manipulate the balloon catheter 28 to "open up" the occluded region 32 in the right coronary artery 34.

The radius of curvature of the guide catheter 10 may not always be as shown in FIG. 3 during stiffening of the shape-memory element 18. In FIG. 3, a tight or acute radius of curvature is illustrated. However, it will be understood that the radius of curvature may vary depending upon the configuration of the guide catheter 10 and the type of intervention (e.g., atherectomy, angioplasty, localized drug delivery, laserplasty, or the like) taking place.

Referring now to FIG. 2, forces 54 and 56 are forces generated by guide catheter 10 pushing against the right coronary ostium 42 and the aortic arch 38, respectively. The values of ostium force 54 and aortic arch force 56 are functions of the specific material in and design of guide catheter 10 and are unchangeable by the physician. Referring now to FIG. 3, by heating the shape-memory tube 18 so that it moves to assume a new position in the heart 30, it is possible to change the shape of tubular member 12 and therefore exert greater forces 54' and 56' on the right coronary ostium 42 and the aortic arch 38. By using control system 20 to regulate the temperature (and shape/modulus) of shape-memory tube 18, it is possible for the physician to control anchoring or wedging action of guide catheter 10 in the aorta. These greater forces 54' and 56' will better "seat" the guide catheter 10 in the aorta when tight lesions in occluded region 32 cause back force on the guide wire 58 and balloon catheter 28.

Guide catheter 10 is configured to provide a flexible device for insertion into the body that also locally bends and changes stiffness (modulus) upon command for added support as other objects are passed through the inner lumen of the guide catheter 10. As these central objects (e.g., guide wire, balloon catheter, atherectomy catheter, etc.) encounter resistance to advancement, they result in a "backout" force which typically causes a conventional guide catheter (not shown) to unseat itself from its original engagement point (e.g., blood vessel ostium 42). A device which could increase in modulus under these conditions (i.e., "get stiffer"), such as guide catheter 10, would enable a physician (or other user) to transmit more forward (axial) force to the guide wire 58, balloon catheter 28, etc. The guide catheter 10 ideally has an ambient modulus that has similar flexibility throughout its length, but when activated has at least one localized section that "stiffens" to hold the guide catheter's position as resistance is encountered by the object(s) being maneuvered within the guide catheter 10.

Figures 4, 5, 6:
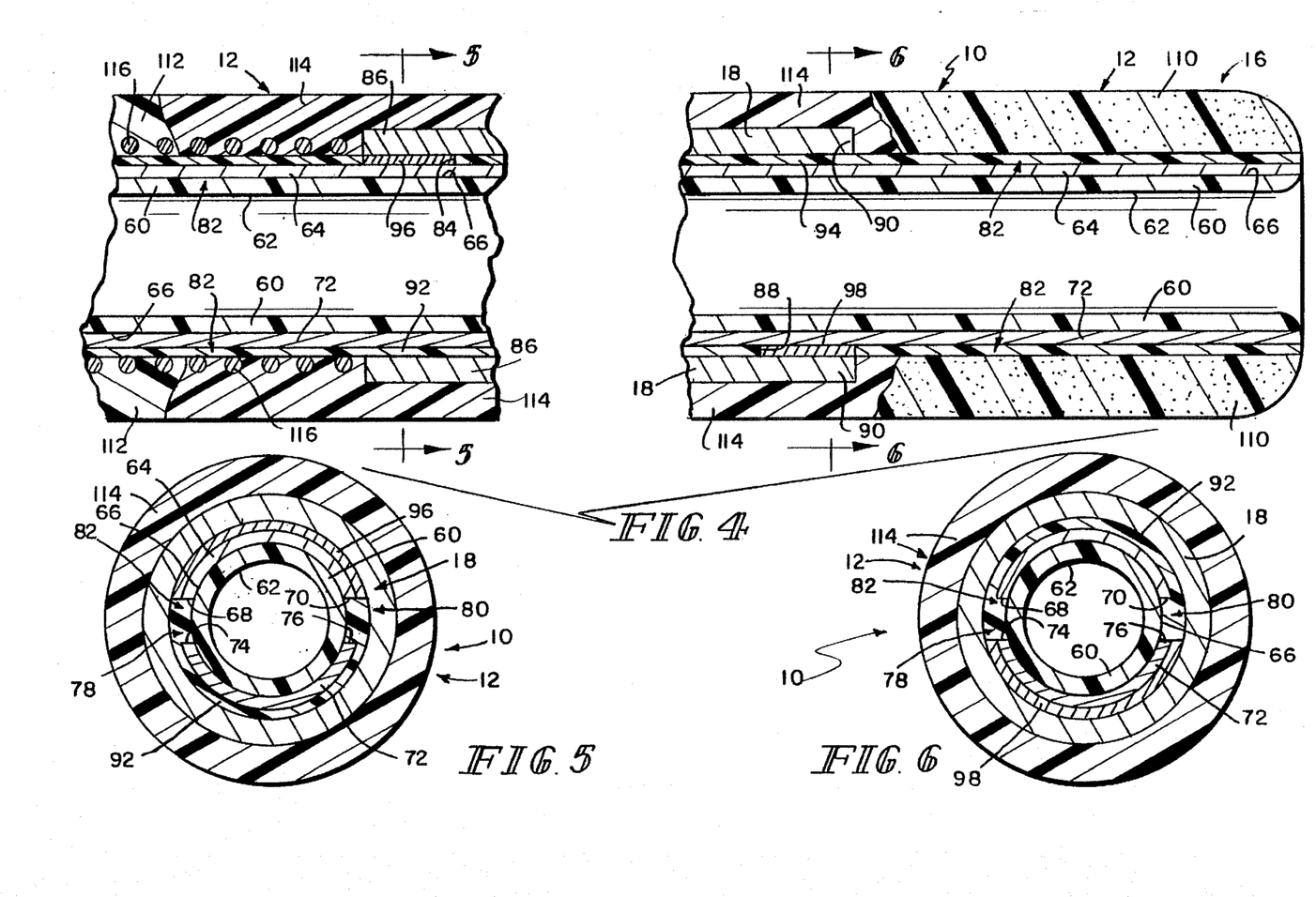
FIG. 4 an enlarged longitudinal sectional view of the guide catheter of FIG. 1 showing an inner liner sleeve, first and second conductive coatings around the liner sleeve, an insulator around the conductive coatings, a braided sleeve around a left-side portion of the insulator, a shape-memory tube around a central portion of the insulator, and an outer tubular member around the braided sleeve, shape-memory tube, and a right-side portion of the insulator.
FIG. 5 is a transverse sectional view taken along line 5—5 of FIG. 4 showing a first C-shaped curved strip made of electrically conductive material lying above the semicircular first conductive coating and communicating electricity from the radially inner first conductive coating to the surrounding radially outer shape-memory tube.
FIG. 6 is a transverse sectional view taken along line 6—6 of FIG. 4 showing a second C-shaped curved strip made of electrically conductive material lying below the semicircular second conductive coating and communicating electricity from the radially inner second conductive coating to the surrounding radially outer shape-memory tube.

Detailed illustrations of the interior components of guide catheter 10 are provided in FIGS. 4–6. Referring now to FIG. 4, guide catheter 10 includes a tubular cylindrical liner sleeve 60 formed to include a lumen 62 for receiving objects such as balloon catheters, etc. therein, the shape-memory tube 18 around the liner sleeve 60, and the tubular member 12 around the liner sleeve 60 and the shape-memory tube 18. Preferably, the liner sleeve 60 is made of a material such as PTFE, PVDF, polyethylene, etc. In one embodiment, liner sleeve 60 is a preformed tubular member configured to support external coatings or other elements during assembly and before the liner sleeve is disposed in a guide catheter or the like. In another embodiment, a suitable liner sleeve can be produced by applying a coating (e.g., an electrically insulating coating) to an interior surface (e.g., a cylindrical interior surface) of a guide catheter or the like.

A first conductive coating 64 is applied to about one half of the exterior surface 66 of liner sleeve 60 as shown in FIGS. 4–6. This first conductive coating 64 has a semicircular transverse cross-sectional shape as shown in FIG. 5 and resembles a thin-walled tubular cylinder cut in half along its length. The first conductive coating 64 also includes spaced-apart first and second longitudinally extending edges 68, 70 as shown in FIG. 5.

A second conductive coating 72 is applied to the other half of the exterior surface 66 of liner sleeve 60 as shown in FIGS. 4–6. This second conductive coating 72 has a semicircular transverse cross-sectional shape as shown in FIGS. 6 and has an elongated thin-walled "hut-like" shape similar to the first conductive coating 64. The second conductive coating 72 also includes spaced-apart first and second longitudinally extending edges 74, 76 as shown in FIG. 5.

The first and second conductive coatings 64, 72 are deposited on the exterior surface 66 of liner sleeve 60 to create two longitudinally extending channels 78, 80. A first longitudinally extending channel 78 is defined between the pair of first longitudinally extending edges 68, 74 and a second longitudinally extending channel 80 is defined between the pair of second longitudinally extending edges 70, 76. Both conductive coatings 64, 72 are illustratively made of copper, silver, or some suitable conductive alloy and have a uniform thickness of about 0.002 inch (0.05 mm).

As an alternative to use of a preformed tubular liner sleeve and deposited conductive coatings, a suitable liner and conductor sub-assembly could be made by first laying two or more pieces of conductive material on an elongated mandrel so that the pieces extend along the longitudinal axis of the mandrel, second applying a suitable coating around the pieces to fixate them, third removing the mandrel from the fixated pieces to expose an interior surface of the fixated pieces, and fourth applying a coating (e.g., an electrically insulative coating) to the interior surface of the fixated pieces to define a liner.

A dielectric coating or insulator 82 is deposited onto the first and second conductive coatings 64, 72 and exposed portions of the liner sleeve 60 (e.g., floors in the first and second longitudinally extending channels 78, 80) to insulate around the first and second conductive coatings 64, 72. This insulator 82 is formed to include a C-shaped first aperture 84 adjacent to an inner end 86 of the shape-memory tube 18 and a C-shaped second aperture 88 adjacent to an outer end 90 of the shape-memory tube 18 as shown in FIG. 4. Preferably, the insulator 82 is made of plastic or other insulative material.

The insulator 82 includes an elongated strip lying in each of the first and second longitudinally extending channels 78, 80 to prevent establishment of electrical communication directly between the first and second conductive coatings 64, 72 as shown in FIGS. 5 and 6. The insulator 82 also prevents unwanted electrical contact between the first conductive coating 64 and the surrounding shape-memory tube 18 as shown in FIGS. 4 and 6. Further, the insulator 82 also prevents unwanted electrical contact between the second conductive coating 72 and the surrounding shape-memory tube 18 as shown in FIGS. 4 and 5. As shown in FIG. 5, the insulator 82 includes a first semicircular strip or first curved end portion 92 that is appended to each elongated strip and positioned to lie in an annular space located between the second conductive coating 72 and the shape-memory tube 18. As shown in FIG. 6, the insulator 82 also includes a second semicircular strip or second curved end portion 94 that is appended to each elongated strip and positioned to lie in an annular space located between the first conductive coating 64 and the shape-memory tube 18.

First and second conductors 96, 98 are positioned inside the lumen 99 of shape-memory tube 18. First conductor 96 carries electric current from first conductive coating 64 to the inner end 86 of shape-memory tube 18. The first conductor 96 is a C-shaped curved strip positioned to lie in the C-shaped first aperture 84 formed in the insulator 82. Second conductor 98 carries electric current from the outer end 90 of shape-memory tube 18 to second conductive coating 72. The second conductor 98 is a C-shaped curved strip positioned to lie in the C-shaped second aperture 88 formed in the insulator 82. Each conductor 96, 98 is illustratively made of a suitable conductive adhesive, weldment, or solder.

As shown in FIG. 4, outer tubular member 12 includes a soft tip 110, a trailing outer sleeve 112, and a leading outer sleeve 114 interconnecting the soft tip 110 and the trailing outer sleeve 112. The soft tip 110 is made of a "soft" material such as plastic, nylon, etc. This material will have a lower durometer (hardness measure) than outer sleeves 112, 114 so that the tip 110 is less traumatic to the endothelial lining of the right coronary ostium 42 that it engages. In addition, the soft tip 110 is preferably radiopaque to make it more visible on a fluoroscope. The outer sleeves 112, 114 are stiffer than the soft tip 110 to achieve smooth transition of torque and bending. A stainless steel braid 116 is positioned around the insulator 82 and inside the outer sleeves 112, 114 as shown in FIG. 4. Leading outer sleeve 114 is preferably nylon or other plastic material that is fused over the exterior surface of shape-memory tube 18 and the distal end (approximately one inch) of braid 116 as shown in FIG. 4. The trailing outer sleeve 112 is preferably made of polyether block amide, nylon, or other plastic material. The outer sleeves 112, 114 function as a plastic top coat of higher durometer (hardness) that is applied over the shape-memory tube 18 and the distal end of the exposed braid 16 to bridge the transition between the shape-memory tube 18 and the braid 16.

Advantageously, guide catheter 10 includes electrical pathways that are applied as coatings 64, 72 on liner sleeve 60. Electrical continuity to raise the nitinol temperature above its activation temperature has typically been imbedded within a conventional "shaft" extrusion, either as separate wires (e.g., a "barber pole-type" wrap) or as two or more of the braid wires. Guide catheter 10 incorporates coating a PTFE, PVDF, PE, etc. liner with a conductive path (e.g., silver, copper, alloy, etc.) and a dielectric coating for electrical insulation.

In addition, guide catheter 10 includes nitinol tube(s) for selectively stiffening a region(s) of the guide catheter 10. Nickel-titanium alloys (as well as others) exhibit shape-memory properties by returning to a previously "taught" shape/position when raised above their activation temperatures. In addition, the elastic modulus (slope of a curve plotting stress vs. strain) increases as the material is heated above its activation temperature. This increase in modulus causes an increase in the bending stiffness of the tube. It is this increase that this stiffenable guide catheter 10 capitalizes upon. Moreover, nitinol tubing 18 offers several advantages over conventional small rectangular or round elements positioned radially about the central catheter axis. Because it is radially continuous, the tubing 18 achieves a higher modulus than smaller, discontinuous elements. Also, the tubing 18 can be concentrically placed about the catheter axis, making it easier to handle and assemble than a number of conventional smaller elements.

Advantageously, the outer tubular member 12 of guide catheter 10 includes a plurality of materials with different hardness durometers. As one moves from the proximal to distal ends of the guide catheter 10, the cross-section changes as internal components begin and end as shown in FIG. 4. As these changes occur (e.g., stainless steel braid 116 ends and nitinol tube 18 begins), a transition zone occurs—additional plastic material is displaced by the nitinol tube 18. To reduce the likelihood of a kink point occurring, a chemically similar, but stiffer, plastic top coat is applied which fuses around the braid 116 and coats the outer surface of the nitinol tube 18. This material change helps bridge the stiffness changes at these types of interfaces.

In the present invention, the electrical pathways for heating the nitinol tube(s) 18 are incorporated as "platings" or "coatings" 64, 62 on the exterior surface 62 of the liner sleeve 60. A dielectric (non-conductive) material 82 is applied over the "plated" material for electrical insulation. Above this dielectric 82, a braid 116 is incorporated and a plastic top coat 112 is applied—the combination of which yields a catheter 10 with acceptable torque transmission from proximal to distal ends.

An initial method of engagement of vessel branches follows the same practice as for other similar devices. However the presence of the nitinol tube(s) 118 allows for the selective "locking" of the catheter tip into the vessel branch. A combination of shape change (shape memory) and stiffness increase results in anchoring the tip 110 into an ostium, side branch, etc. This "locking" can be disengaged by the user (e.g., physician) returning the guide catheter 110 to the original flexible device for removal, repositioning, etc.

Figures 7, 8, 9:
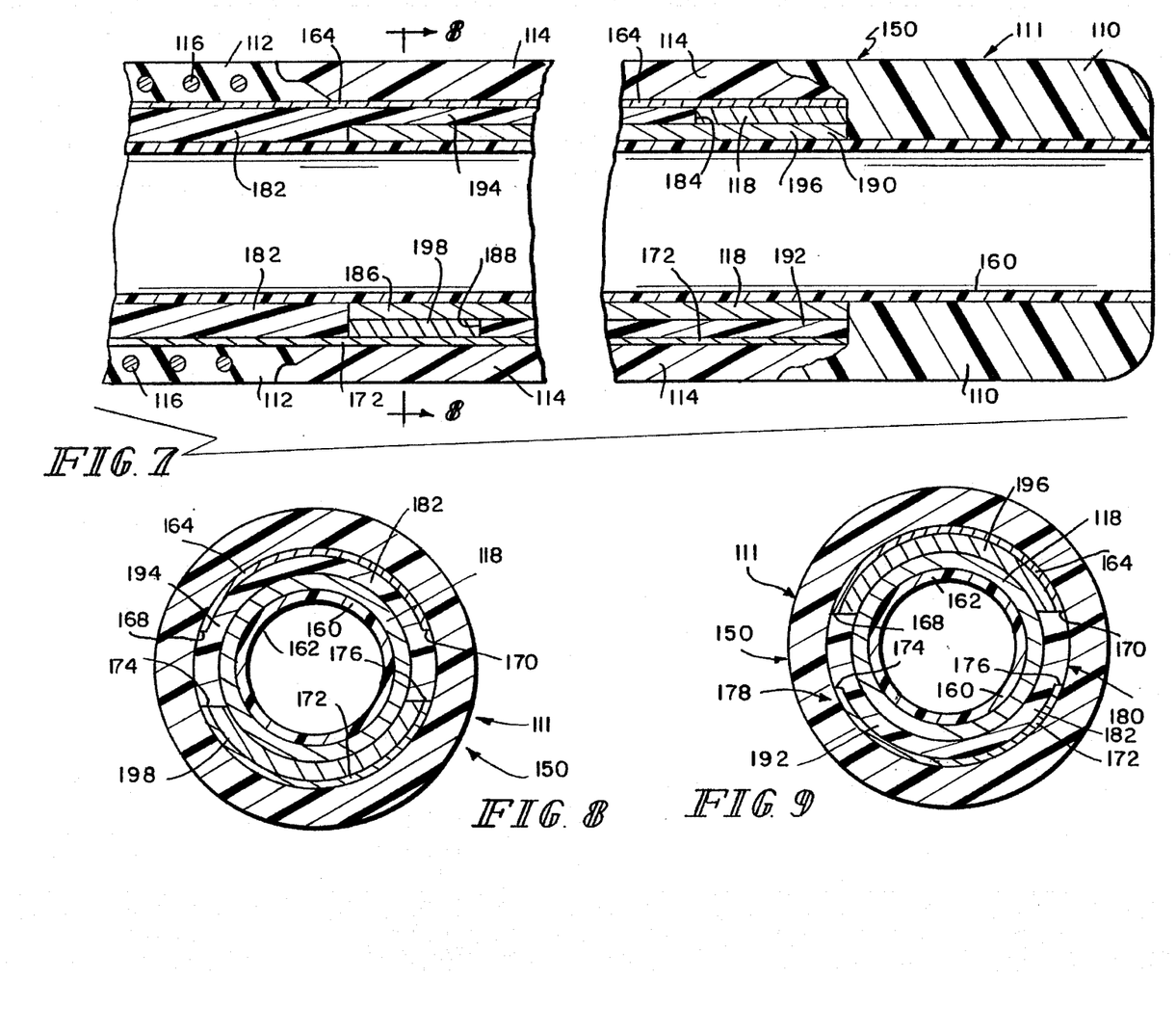
FIG. 7 is a view of a second embodiment of an apparatus in accordance with the present invention similar to FIG. 5.
FIG. 8 is a transverse sectional view taken along line 8—8 of FIG. 7.
FIG. 9 is a transverse sectional view taken along line 9—9 of FIG. 7.

Detailed illustrations of the interior components of another guide catheter 150 in accordance with the present invention are provided in FIGS. 7–9. Referring now to FIG. 7, guide catheter 150 includes a tubular cylindrical liner sleeve 160 formed to include a lumen 162 for receiving objects such as balloon catheters, etc. therein, a shape-memory tube 118 around the liner sleeve 160, and a tubular member 111 around the liner sleeve 160 and the shape-memory tube 118. Preferably, the liner sleeve 160 is made of a material such as PTFE, PVDF, polyethylene, etc.

A first conductive coating 164 extends about one-half of the exterior surface of insulator 182 as shown in FIGS. 7–9. This first conductive coating 164 has a semicircular transverse cross-sectional shape as shown in FIG. 8 and resembles a thin-walled tubular cylinder cut in half along its length. The first conductive coating 164 also includes spaced-apart first and second longitudinally extending edges 168, 170 as shown in FIG. 8.

A second conductive coating 172 extends about the other half of insulator 182 as shown in FIGS. 7–9. This second conductive coating 172 has a semicircular transverse cross-sectional shape as shown in FIG. 9 and has an elongated thin-walled "hut-like" shape similar to the first conductive coating 164. The second conductive coating 172 also includes spaced-apart first and second longitudinally extending edges 174, 176 as shown in FIG. 8.

The first and second conductive coatings 164, 172 are arranged to create two longitudinally extending channels 178, 180. A first longitudinally extending channel 178 is defined between the pair of first longitudinally extending edges 168, 174 and a second longitudinally extending channel 180 is defined between the pair of second longitudinally extending edges 170, 176. Both conductive coatings 164, 172 are illustratively made of copper, silver, or some suitable conductive alloy and have a uniform thickness of about 0.002 inch (0.05 mm).

A dielectric coating or insulator 182 is deposited onto portions of the exterior surface of the shape-memory tube 118 and exposed portions of the liner sleeve 160 to insulate underneath the first and second conductive coatings 164, 172. This insulator 182 is formed to include a C-shaped first aperture 184 adjacent to an outer end 190 of the shape-memory tube 118 and a C-shaped second aperture 188 adjacent to an inner end 186 of the shape-memory tube 118 as shown in FIG. 7. Preferably, the insulator 182 is made of plastic or other insulative material.

The insulator 182 includes an elongated strip lying in each of the first and second longitudinally extending channels 178, 180 to prevent establishment of electrical communication directly between the first and second conductive coatings 164, 172 as shown in FIGS. 8 and 9. The insulator 182 also prevents unwanted electrical contact between shape-memory tube 118 and the surrounding first conductive coating 64 as shown in FIGS. 7 and 8. Further, the insulator 182 also prevents unwanted electrical contact between shape-memory tube 118 and the surrounding second conductive coating 172 as shown in FIGS. 7 and 9. As shown in FIG. 9, the insulator 182 includes a first semicircular strip or first curved end portion 192 that is appended to each elongated strip and positioned to lie in an annular space located between the second conductive coating 172 and the shape-memory tube 118. As shown in FIG. 8, the insulator 182 also includes a second semicircular strip or second curved end portion 194 that is appended to each elongated strip and positioned to lie in an annular space located between the first conductive coating 164 and the shape-memory tube 118.

First and second conductors 196, 198 are positioned around portions of the cylindrical exterior surface of shape-memory tube 118 as shown best in FIGS. 8 and 9. First conductor 196 carries electric current from first conductive coating 164 to the outer end 190 of shape-memory tube 118. The first conductor 196 is a C-shaped curved strip positioned to lie in the C-shaped first aperture 184 formed in the insulator 182. Second conductor 198 carries electric current from the inner end 186 of shape-memory tube 118 to second conductive coating 172. The second conductor 198 is a C-shaped curved strip positioned to lie in the C-shaped second aperture 188 formed in the insulator 182. Each conductor 196, 198 is illustratively made of a suitable conductive adhesive, weldment, or solder.

As shown in FIG. 7, outer tubular member 111 includes soft tube 110, trailing outer sleeve 112, and leading outer sleeve 114 interconnecting the soft tip 110 and the trailing outer sleeve 112. As noted previously, soft tip 110 is made of a "soft" material such as plastic, nylon, etc. This material will have a lower durometer (hardness measure) than outer sleeves 112, 114 so that the tip 110 is less traumatic to the endothelial lining of the right coronary ostium 42 that it engages. In addition, the soft tip 110 is preferably radiopaque to make it more visible on a fluoroscope. The outer sleeves 112, 114 are stiffer than the soft tip 110 to achieve smooth transition of torque and bending. A stainless steel braid 116 is positioned around the first and second conductive coatings 164, 172 and insulator 182 and inside the outer sleeve 112 as shown in FIG. 7. Leading outer sleeve 114 is preferably nylon or other plastic material that is fused over the exterior surface of insulator 182, first conductor 196, and second conductor 198 as shown in FIG. 7. The trailing outer sleeve 112 is preferably made of polyether block amide, nylon, or other plastic material.

Although the invention has been described in detail with reference to the illustrated preferred embodiment, variations and modifications exist within the scope and spirit of the invention as defined in the following claims.

We claim:

1. An apparatus comprising
a flexible, elongated tubular member having a central axis extending therethrough,
a shape-memory tube made of temperature-activated shape-memory material and formed to include a lumen extending therethrough, the shape-memory tube being arranged in the tubular member to cause the lumen to extend along the central axis of the tubular member,
a liner sleeve positioned to extend through the lumen of the shape-memory tube and lie inside the tubular member, the liner sleeve being configured to have an annular exterior surface, and
control means for selectively heating the shape-memory tube to move the shape-memory tube to assume a stiff predetermined shape, thereby stiffening and moving the tubular member so that it moves toward a corresponding predetermined shape, the control means including a first electrically conductive coating around the liner sleeve, a second electrically conductive coating around the liner sleeve and positioned to lie in spaced-apart relation to the first electrically conductive coating, insulator means for preventing establishment of an electrical connection between the shape-memory tube and each of the first and second electrically conductive coatings, the insulator means being positioned to lie around the annular exterior surface of the liner sleeve and formed to include first and second openings, first conductor means passing through the first opening in the insulator means for electrically connecting the first electrically conductive coating to the shape-memory tube, and second conductor means passing through the second opening in the insulator means for electrically connecting the shape-memory tube to the second electrically conductive coating.

2. The apparatus of claim 1, wherein the liner sleeve and the shape-memory tube cooperate to define an annular space therebetween, the first electrically conductive coating is affixed to the liner sleeve, the second electrically conductive coating is affixed to the liner sleeve, and the insulator means is disposed in the annular space to lie around the first and second electrically conductive coatings and inside the lumen of the shape-memory tube.

3. The apparatus of claim 2, wherein the shape-memory tube has a cylindrical interior surface, the first electrically conductive coating has a concave interior surface affixed to the liner sleeve and a convex exterior surface facing toward the cylindrical interior surface of the shape-memory tube, and the first conductor means lies in said annular space and interconnects the convex exterior surface and the cylindrical interior surface.

4. The apparatus of claim 3, wherein the first conductor means is a curved strip of electrically conductive material.

5. The apparatus of claim 3, wherein the liner sleeve has an elongated cylindrical surface having a circumference and the first conductor means is a C-shaped curved strip positioned to extend around a semicircular portion of the circumference of the cylindrical exterior surface of the liner sleeve.

6. The apparatus of claim 3, wherein the first conductor means is formed of an electrically conductive material.

7. The apparatus of claim 3, wherein the second electrically conductive coating has a concave interior surface affixed to the liner sleeve and a convex exterior surface facing toward the cylindrical inner surface of the shape-memory tube and the second conductor means lies in said annular space in spaced-apart relation to the first conductor means and interconnects the convex exterior surface of the second electrically conductive coating and the cylindrical interior surface of the shape-memory tube.

8. The apparatus of claim 7, wherein the liner sleeve has an elongated cylindrical exterior surface having a circumference, the first conductor means is a C-shaped curved strip positioned to extend around a semicircular portion of the circumference of the cylindrical exterior surface of the liner sleeve, and the second conductor means is another C-shaped curved strip positioned to extend around an opposite semicircular portion of the circumference of the cylindrical exterior surface of the liner sleeve.

9. The apparatus of claim 7, wherein the shape-memory tube has spaced-apart first and second ends, the first conductor means is a first curved strip engaging the first end, and the second conductor means is a second curved strip engaging the second end.

10. The apparatus of claim 7, wherein the first conductor means is a first curved strip having first and second longitudinally extending edges and the insulator means includes a first curved end portion interconnecting the first and second longitudinally extending edges of the first curved strip and contacting both of the convex exterior surface of the second electrically conductive coating and the cylindrical interior surface of the shape-memory tube.

11. The apparatus of claim 10, wherein the second conductor means is a second curved strip having first and second longitudinally extending edges and the insulator means includes a second curved end portion interconnecting the first and second longitudinally extending edges of the second curved strip and contacting both of the convex exterior surface of the first electrically conductive coating and the cylindrical interior surface of the shape-memory tube and an elongated middle portion interconnecting the first and second curved end portions and contacting the convex exterior surfaces of the first and second electrically conductive coatings and the cylindrical interior surface of the shape-memory tube.

12. The apparatus of claim 1, wherein the first electrically conductive coating has a semicircular transverse cross-sectional shape.

13. The apparatus of claim 12, wherein the second electrically conductive coating has a semicircular transverse cross-sectional shape.

14. The apparatus of claim 1, wherein the insulator means is a cylindrical coating made of a dielectric material.

15. The apparatus of claim 14, wherein the insulator means is formed to position the first opening inside the lumen of the shape-memory tube and adjacent to one end of the shape-memory tube and to position the second opening inside the lumen of the shape-memory tube and adjacent to an opposite end of the shape-memory tube.

16. The apparatus of claim 1, wherein the first electrically conductive coating has a semicircular transverse cross-sectional shape and spaced-apart first and second longitudinally extending edges passing through the lumen of the shape-memory tube and adjacent to the liner sleeve, the second electrically conductive coating has a semicircular transverse cross-sectional shape and spaced-apart first and second longitudinally extending edges passing through the lumen of the shape-memory tube and adjacent to the liner sleeve, the first longitudinally extending edges of each of the first and second electrically conductive coatings are spaced apart to define a first longitudinally extending channel along an exterior surface of the liner sleeve, the second longitudinally extending edges of each of the first and second electrically conductive coatings are spaced apart to define a second longitudinally channel along an opposite side of the exterior surface of the liner sleeve, and the insulator means includes an elongated strip lying in each of the first and second longitudinally extending channels.

17. The apparatus of claim 16, wherein the second electrically conductive coating and the shape-memory tube are positioned to define an annular space therebetween, the first electrically conductive coating and the shape-memory tube are positioned to define another annular space therebetween, and the insulator means further includes a first curved end portion appended to each elongated strip and positioned to lie in the annular space located between the second electrically conductive coating and the shape-memory tube and a second curved end portion appended to each elongated strip and positioned to lie in said another annular space located between the first electrically conductive coating and the shape-memory tube.

18. The apparatus of claim 1, wherein the tubular member includes a distal tip positioned to lie in axially spaced-apart relation to the shape-memory tube and a tube-covering portion abutting the distal tip and containing the shape-memory tube therein, the distal tip is made of a first material having a first hardness, and the tube-covering portion is made of a second material having a second hardness greater than the first hardness.

19. The apparatus of claim 18, wherein the tubular member further includes a base portion lying in spaced-apart relation to the distal tip to position the tube-covering portion between the distal tip and the base portion and the base portion is made of a third material having a third hardness greater than the second hardness.

20. The apparatus of claim 19, further comprising a tubular braided sleeve formed to include a lumen receiving at least the liner sleeve therein and wherein the tubular braid sleeve includes an axially forward portion disposed in the tube-covering portion of the tubular member and an axially rearward portion disposed in the base portion of the tubular member.

21. The apparatus of claim 1, wherein the insulator means is formed to include an interior region receiving the shape-memory tube therein.

22. An apparatus comprising an inner tubular member, a first electrically conductive coating positioned to lie on an exterior surface of the inner tubular member, a second electrically conductive coating positioned to lie on the exterior surface of the inner tubular member in spaced-apart relation to the first electrically conductive coating, a shape-memory tube made of temperature-activated shape-memory material and formed to include a lumen extending therethrough, the inner tubular member and the first and second electrically conductive coatings extending through the lumen of the shape-memory tube, means for coupling the shape-memory tube to the first and second electrically conductive coatings to establish an electrical circuit including in series a first conductive path through the first electrically conductive coating, a second conductive path through the shape-memory tube, and a third conductive path through the second electrically conductive coating, an outer tubular member formed to include a lumen receiving the inner tubular member, the first and second electrically conductive coatings, the shape memory tube, and the coupling means therein, and control means for applying an electrical potential to the first and second electrically conductive coatings to pass an electric current through the second conductive path through the shape-memory tube to heat the shape-memory tube so that the shape-memory tube moves toward a predetermined shape, thereby moving the outer tubular member toward a corresponding predetermined shape.

23. The apparatus of claim 22, wherein the first electrically conductive coating has a semicircular transverse cross-sectional shape.

24. The apparatus of claim 23, wherein the second electrically conductive coating has a semicircular transverse cross-sectional shape.

25. The apparatus of claim 22, wherein the shape-memory tube has a cylindrical interior surface and the first electrically conductive coating has a concave interior surface affixed to the exterior surface of the inner tubular member and a convex exterior surface facing toward the cylindrical interior surface of the shape-memory tube.

26. The apparatus of claim 25, wherein the coupling means is positioned to lie in said annular space and inside the lumen of the shape-memory tube.

27. The apparatus of claim 25, wherein the second electrically conductive coating has a concave interior surface affixed to the exterior surface of the tubular member and a convex exterior surface facing toward the cylindrical interior surface of the shape-memory tube.

28. The apparatus of claim 27, wherein the first and second electrically conductive coatings and the shape-memory tube cooperate to define an annular space therebetween and the coupling means is positioned to lie in said annular space and inside the lumen of the shape-memory tube.

29. The apparatus of claim 22, wherein the coupling means includes first conductor means for electrically connecting the first electrically conductive coating to the shape-memory tube, second conductor means for electrically connecting the second electrically conductive coating to the shape-memory tube, and an insulator between the shape-memory tube and each of the first and second conductor means.

30. The apparatus of claim 29, wherein the first conductor means is a curved strip of electrically conductive material.

31. The apparatus of claim 29, wherein the inner tubular member has an elongated cylindrical surface having a circumference and the first conductor means is a C-shaped curved strip positioned to extend around a semicircular portion of the circumference of the cylindrical exterior surface of the inner tubular member.

32. The apparatus of claim 29, wherein the first conductor means is formed of an electrically conductive material.

33. The apparatus of claim 29, wherein the liner sleeve has an elongated cylindrical exterior surface having a circumference, the first conductor means is a C-shaped curved strip positioned to extend around a semicircular portion of the circumference of the cylindrical exterior surface of the liner sleeve, and the second conductor means is another C-shaped curved strip positioned to extend around an opposite semicircular portion of the circumference of the cylindrical exterior surface of the liner sleeve.

34. The apparatus of claim 29, wherein the first conductor means is a first curved strip having first and second longitudinally extending edges and the insulator includes a first curved end portion interconnecting the first and second longitudinally extending edges of the first curved strip and contacting both of the convex exterior surface of the second electrically conductive coating and the cylindrical interior surface of the shape-memory tube.

35. The apparatus of claim 34, wherein the second conductor means is a second curved strip having first and second longitudinally extending edges and the insulator includes a second curved end portion interconnecting the first and second longitudinally extending edges of the second curved strip and contacting both of the convex exterior surface of the first electrically conductive coating and the cylindrical interior surface of the shape-memory tube and an elongated middle portion interconnecting the first and second curved end portions and contacting the convex exterior surfaces of the first and second electrically conductive coatings and the cylindrical interior surface of the shape-memory tube.

36. An apparatus comprising
a shape-memory tube made of shape-memory material and formed to include a lumen extending therethrough,
an inner tubular member extending through the lumen of the shape-memory tube,
a first electrically conductive coating on the inner tubular member,
a second electrically conductive coating on the inner tubular member,
a dielectric coating lying in the lumen of the shape-memory tube and electrically separating the first and second electrically conductive coating from one another and from the shape-memory tube,
a first electrical conductor interconnecting the first electrically conductive coating and the shape-memory tube and passing through the dielectric coating,
a second electrical conductor interconnecting the second electrically conductive coating and the shape-memory tube and passing through the dielectric coating, and
an outer tubular member formed to include a lumen receiving the inner tubular member, the first and second electrically conductive coatings, the dielectric coating, the first and second electrical conductors, and the shape-memory tube.

37. The apparatus of claim 36, wherein the first and second electrical conductors are positioned to lie in the lumen of the shape-memory tube.

38. The apparatus of claim 37, wherein at least one of the first and second electrical conductors is a curved strip of electrically conductive material.

39. The apparatus of claim 37, wherein at least one of the electrical conductors is formed of an electrically conductive material.

40. The apparatus of claim 36, wherein the first electrically conductive coating has a semicircular transverse cross-sectional shape.

41. The apparatus of claim 40, wherein the second electrically conductive coating has a semicircular transverse cross-sectional shape.

42. The apparatus of claim 36, wherein the inner tubular member has an elongated cylindrical surface having a circumference and the first electrical conductor is a C-shaped curved strip positioned to extend around a semicircular portion of the circumference of the cylindrical exterior surface of the inner tubular member.

43. An apparatus comprising
a flexible, elongated tubular member having a central axis extending therethrough,
a shape-memory tube made of temperature-activated shape-memory material and formed to include a lumen extending therethrough, the shape-memory tube being arranged in the tubular member to cause the lumen to extend along the central axis of the tubular member, the shape-memory tube having a certain modulus of elasticity at a predetermined temperature,
a liner sleeve positioned to extend through the lumen of the shape-memory tube and lie inside the tubular member, the liner sleeve being configured to have an annular exterior surface, and
control means for selectively heating the shape-memory tube to a temperature in excess of the predetermined temperature to stiffen the shape-memory tube so that it has a modulus of elasticity that is greater than the certain modulus of elasticity and assumes a stiff predetermined shape, thereby stiffening the tubular member, the control means including a first electrically conductive coating around the liner sleeve, a second electrically conductive coating around the liner sleeve and positioned to lie in spaced-apart relation to the first electrically conductive coating, insulator means for preventing establishment of an electrical connection between the shape-memory tube and each of the first and second electrically conductive coatings, the insulator means being positioned to lie around the annular exterior surface of the liner sleeve and formed to include first and second openings, first conductor means passing through the first opening in the insulator means for electrically connecting the first electrically conductive coating to the shape-memory tube, and second conductor means passing through the second opening in the insulator means for electrically connecting the shape-memory tube to the second electrically conductive coating.

44. The apparatus of claim 43, wherein the liner sleeve and the shape-memory tube cooperate to define an annular space therebetween, the first electrically conductive coating is affixed to the liner sleeve, the second electrically conductive coating is affixed to the liner sleeve, and the insulator means is disposed in the annular space to lie around the first and second electrically conductive coatings and inside the lumen of the shape-memory tube.

45. The apparatus of claim 43, wherein the first electrically conductive coating has a semicircular transverse cross-sectional shape.

46. The apparatus of claim 45, wherein the second electrically conductive coating has a semicircular transverse cross-sectional shape.

47. The apparatus of claim 43, wherein the insulator means is a cylindrical coating made of a dielectric material.

48. The apparatus of claim 43, wherein the first electrically conductive coating has a semicircular transverse cross-sectional shape and spaced-apart first and second longitudinally extending edges passing through the lumen of the shape-memory tube and adjacent to the liner sleeve, the second electrically conductive coating has a semicircular transverse cross-sectional shape and spaced-apart first and second longitudinally extending edges passing through the lumen of the shape-memory tube and adjacent to the liner sleeve, the first longitudinally extending edges of each of the first and second electrically conductive coatings are spaced apart to define a first longitudinally extending channel along an exterior surface of the liner sleeve, the second longitudinally extending edges of each of the first and second electrically conductive coatings are spaced apart to define a second longitudinally channel along an opposite side of the exterior surface of the liner sleeve, and the insulator means includes an elongated strip lying in each of the first and second longitudinally extending channels.

49. The apparatus of claim 43, wherein the tubular member includes a distal tip positioned to lie in axially spaced-apart relation to the shape-memory tube and a tube-covering portion abutting the distal tip and containing the shape-memory tube therein, the distal tip is made of a first material having a first hardness, and the tube-covering portion is made of a second material having a second hardness greater than the first hardness.

50. The apparatus of claim 43, wherein the insulator means is formed to include an interior region receiving the shape-memory tube therein.

* * * * *